United States Patent [19]

Neufeld

[11] Patent Number: 5,488,050
[45] Date of Patent: Jan. 30, 1996

[54] METHODS AND PRODUCTS FOR TREATING PRESBYOPIA

[75] Inventor: Arthur H. Neufeld, Andover, Mass.

[73] Assignee: Telor Ophthalmic Pharmaceuticals, Inc., Woburn, Mass.

[21] Appl. No.: 154,396

[22] Filed: Nov. 18, 1993

Related U.S. Application Data

[63] Continuation of Ser. No. 907,875, Jul. 2, 1992, abandoned.

[51] Int. Cl.$^6$ .................. A61K 31/535; A61K 31/47; A61K 31/41; A61K 31/425
[52] U.S. Cl. .................. 514/236.2; 514/313; 514/359; 514/369; 514/469; 514/492; 514/596; 514/603; 514/630; 514/653; 514/912
[58] Field of Search .................. 514/236.2, 912, 514/313, 359, 369, 469, 492, 596, 603, 630, 653

[56] References Cited

U.S. PATENT DOCUMENTS

| | | | |
|---|---|---|---|
| 4,443,441 | 4/1984 | Galin | 424/244 |
| 4,459,292 | 7/1984 | Andermann et al. | 424/180 |
| 4,496,558 | 7/1985 | DeMarinis et al. | 514/213 |
| 4,797,422 | 1/1989 | Testa | 514/912 |

FOREIGN PATENT DOCUMENTS 2638356  10/1988  France.

OTHER PUBLICATIONS

Hurwitz, B., et al., "The Effects of the Sympathetic Nervous System on Accommodation", Arch Ophthal, 87, Jun. 1972, pp. 668–674.
Cogan, D., "Accommodation and the Autonomic Nervous System", Arch Ophthal., vol. 18, (1937), pp. 739–766.
Stephens, K., "Effect of the Sympathetic Nervous System on Accommodation", Amer. J. Optometry & Physiol. Optics, vol. 62, No. 6, pp. 402–406 (1985).
Eskridge, J., "Review of Ciliary Muscle Effort in Presbyopia", Amer. J. Optometry & Physiol. Optics, vol. 61, No. 2, pp. 133–138, (1984).
Coleman, A., "Cardiovascular and Intraocular Pressure Effects and Plasma Concentrations of Apraclonidine", Arch Ophthalmol., vol. 108, Sep. 1990.
Robin, A., "Effects of ALO 2145 on Intraocular Pressure Following Argon Laser Trabeculoplasty", Arch Ophthalmol., vol. 105, May 1987, pp. 646–650.
Jampel, H., "Apraclonidine", Arch Ophthalmol, vol. 106, Aug. 1988, pp. 1069–1073.
Abrams, D., "The Safety and Efficacy of Topical 1% ALO 2145 . . . ", Arch Ophthalmol, vol. 105, Sep. 1987, pp. 1205–1207.
Samson, C. R., "Safety and toleration of oxymetazoline ophthalmic solution", Pharmatherapeutica, vol. 2, No. 6, 1980, pp. 347–352.
Duzman, E., "Topically Applied Oxymetazoline", Arch Ophthalmol., vol. 101, Jul. 1983, pp. 1122–1126.
Duzman, E., "Efficacy and Safety of Topical Oxymetazoline in Treating Allergic and Environmental Conjunctivitis", Ann. Ophthalmol 1986; 18: 28–31.
Abelson, M., "Tolerance and Absence of Rebound Vasodilation Following Topical Ocular Decongestant Usage", pp. 1364–1367, 1983.
Hurwitz, P., "Uses of Naphazoline (Privine) in Ophthalmology", Arch Ophthalmol 1950; 43; pp. 712–717.
Podos, S., "Experimental compounds to lower intraocular pressure" Australian & New Zealand J. Ophthalmology, 1989; 17(20, pp. 129–135.
Potter, D., "Medetomidine–Induced Alterations of Intraocular Pressure . . . . ", Investigative Ophthal & Visual Science, vol. 32, No. 10, Sep. 1991, pp. 2799–2805.
Rosenfield, M., "The influence of alpha–adrenergic agents on tonic acommodation", Current Eye Research, vol. 9, No. 3, 1990, pp. 267–272.
Serle, J. et al., "Selective α2–Adrenergic Agonists B–HT 920 and UK14304–18", Arch Ophthalmol, vol. 109, Aug. 1991, pp. 1158–1162.
Zetterstrom, C. et al., "Pharmacological Characterization of Human Ciliary Muscle Adrenoceptors in Vitro", Exp. Eye Res. 1988 46: pp. 421–430.
Vartiainen, J. et al., "Dexmedetomidine–Induced Ocular Hypotension in Rabbits With Normal or Elevated Intraocular Pressures", Investigative & Ophthalmol. & Visual Science, vol. 33, No. 6, May 1992, pp. 2019–2023.
Gilmartin, B. et al., "Pharmacological Effects on Accommodative Adaption", Optometry and Vision Science, vol. 69, No. 4, pp. 276–282 (1992).
Gilmartin, B., "A Review of the Role of Sympathetic Innervation of the Ciliary Muscle in Ocular Accommodation", Ophthal, Physiol. Opt. vol. 6, No. 1, pp. 23–37, 1986.
Eskridge, J. B., "Ciliary Muscle effort in presbyopia", J. Optom. Arch, Am. Acad. Opt., Aug. (1972).
Montgomery, D., et al., "Pupil Dilatation with Tropicamide. The Effects on Acuity, Accommodation and Refraction", Eye (1989) 3: pp. 845–848.
Garner, et al., "The Effect of Phenylephrine Hydrochloride on the Resting Point of Accommodation", Investigative Opth. and Visual Science, vol. 24/4, Apr. 1983.
C. Flugel, et al., "Histochemical Differences Within the Ciliary Muscle and its Function in Accommodation", Ex. Eye Res. (1990): 50, pp. 219–226.\

(List continued on next page.)

*Primary Examiner*—Zohreh Fay
*Attorney, Agent, or Firm*—Wolf, Greenfield & Sacks

[57] ABSTRACT

This invention is directed to treatment for increasing the accommodative ability of the eye, for the purpose of decreasing the severity of clinically evident presbyopia, an age-related loss of accommodative ability. The compounds and methods of the invention act by decreasing the tone of parts of the ciliary muscle which act to decrease accommodation, thereby increasing the contractile force of the remaining ciliary muscle, with resultant increased accommodative function.

64 Claims, No Drawings

OTHER PUBLICATIONS

Erickson—Lamy, et al., "Dissociation Between the Effect of Aceclidine on Outflow Facility and Accommodation", 1990 Academic Press Limited.

Diane D., et al., "Ocular Bio Distrib. of Clonidine After Topical Appl. with Ophthalmic Rods or Solution", Jnl. of Ocular Pharma., vol. 5, No. 2, 1989.

van Pinxteren, P. C. M., "Hypotensive Effects after Topical and Intra-Arterial Administration of α-Adrenergic Agonists in Isolated Perfused Rabbit Eyes", Ophthalmic Res., 17: pp. 349–353 (1985).

Elena, et al., "Alph$_2$–Adrenergic Receptors in Rat and Rabbit Eye: A Tritium–Sensitive Film Autoradiography", Ophthalmic Res., 1989; 21:309–314.

Bito, Laszlo, Z., "Presbyopia", Arch Ophthalmol, vol. 106, Nov. 1988.

Rubin, et al., "Pharmacodynamic Studies with a Specific α-Adrenoceptor Agonist (BHT-933) in Man, Jrnl. of Cardio. Pharmacology", pp, 527–530, 1982.

Adler—Grinberg, D., "Questioning Our Classical Understanding of Accommodation and Presbyopia", Am. J. Optom. & Physiol. Optics, vol. 63, No. 7, pp. 571–580 (1986).

Fisher, R. F., "The Mechanics of Accommodation in Relation to Presbyopia", Eye (1988), 2, pp. 646–649.

Gilmartin, B., et al., "The Relationship between Tonic Accommodation and Ciliary Muscle Innervation", Invest. Ophthal. & Visual Science, Jul. 1985, vol. 26, pp. 1024–1028.

Koretz, J. F., et al., "Accommodation and Presbyopia in the Human Eye–Aging of the Anterior Segment", Vision Res., vol. 29, No. 12, pp. 1685–1692, 1989.

Lograno, M. D., et al., "Receptor–responses in fresh human ciliary muscle", Br. J. Pharmac. (1986), 87, pp. 379–385.

van Alphen, "The adrenergic receptors of the intraocular muscles of the human eye", Investigative Ophthalmology, vol. 15, No. 6, pp. 502–505 (Jun. 1976).

Wand, M., et al., "Thymoxamine Hydrochloride: An Alpha–adrenergic Blocker", Survey of Ophthalmology, vol. 25, No. 2, Sep.–Oct. 1980, pp. 75–84.

Zetterstrom, C., "The effects of thymoxamine, phenylephrine and cyclopentolate on the accommodative process in man", Acta Ophthalmologica, 65 (1987) pp. 699–704.

Stark, L. 1988, "Presbyopia in light of accommodation", Am. J. Optom. Physiol. Opt. 65: pp. 407–416.

Gilmartin, B., et al., "The Effect of Timolol Maleate on Tonic Accommodaiton...", Investigative Ophthalmology & Visual Science, vol. 25, Jun. 1984, pp. 763–770.

Zetterstrom, C.; The Effect of Phenylephrine on the Accommodation Process in Man, pp. 872–878; Acta Ophthalmologica V. 62, No. 6; 1984.

T. Miwa et al.; "The Effect of Sympathomimetic and Sympatholytic Drugs Upon Resting Point of Accomodation", 1988, pp. 1235–1241; Acta Soc. Ophthalmol. Jpn. vol. 92, No. 7.

Zetterstrom, C., The effects of thyomoxamine, phenylephrine and cyclopentolate on the accomodative process in man; 1987; pp. 699–704; Acta Ophthalm., v. 65, No. 6.

G. Nyberg; "The Influence of Beta–Adrenoceptor Agonists on Accomodation of the Lens"; 1976; pp. 493–495; Clin. Exp. Pharmacol Physiol.; vol. 3, No. 5.

Zetterstrom, C.; Effects of adrenergic drugs on accomodation and distant refraction in daylight and darkness; 1988; pp. 58–64; v. 66, No. 1.

T. Yoshitomi et al., "Pre–Synaptic Actions of Noradrenaline on the Dog Ciliar Muscle Tissue"; 1986; pp. 119–127; Exp. Eye Res. vol. 43, No. 1.

METHODS AND PRODUCTS FOR TREATING PRESBYOPIA

This application is a continuation of application Ser. No. 07/907,875, filed Jul. 2, 1992, now abandoned.

BACKGROUND OF THE INVENTION

Presbyopia, or age-related loss of accommodative ability, is a very common ocular pathology. Accommodative ability refers to the capacity of the eye to focus for near vision by changing the shape of the lens to become more convex. The ocular tissues involved in the accommodative response include the lens, the zonules (suspensory ligaments) of the lens, and the ciliary muscle. These structures function together in accommodating the eye for focusing on close objects.

Within the eye, the lens is centrally suspended between the anterior and posterior chambers, behind the pupillary opening of the iris. The lens is supported by a radially oriented array of zonules which extend from the lateral edges of the lens to the inner border of the circumferential ciliary muscle. The ciliary muscle is attached to the scleral coat of the eye.

At rest, the eye is focused for distant vision with the lens held in a somewhat flattened, or slightly convex, shape by tension exerted on its periphery by the zonules. These ligaments pull the edges of the lens towards the ciliary body. During accommodation, the shape of the lens becomes more convex. This action is achieved through contraction of the ciliary muscle which allows the ciliary attachment of the zonules to move inward towards the lens, thereby reducing the tension in the zonules. This reduction in tension allows the lens to increase in convexity, resulting in an increase in dioptric power which enables near objects to be imaged clearly on the retina.

Loss of accommodative ability can be measured as the progressive regression of the near point of accommodation, which is the closest point for which the eye can accommodate so that a clear image is formed on the retina. The near point of accommodation is nearest to the eye in the young and recedes gradually until about the age of 45 years, when a much more rapid recession of the near point ensues. This recession continues unabated until about the age of 60 years, by which time all accommodation has been lost.

The amplitude of accommodation may also be quantified by measuring the dioptric power of the eye, a measure of refractive power. The dioptric power is measured in diopters (D). Accomodative ability is greatest in childhood and slowly decreases until it is lost in middle age. At the age of 8 years the dioptric power of the eye can be raised by accommodation to approximately 14 D; at the age of 20 years this has fallen to 11 D. At the age of 30 years the eye can accommodate 9 D. By the age of 50 years, less than 2 D remain.

By the age at which the loss of the amplitude of accommodation has made the near point so far removed that the subject cannot read fine print, the eye has become presbyopic. Presbyopia is the age-related recession of the near point of accommodation, and usually is evident by the age of 45 years. In an otherwise normal eye, convex glasses are prescribed to correct for the decrease in the accommodative power of the lens. In a myope, bifocals will be needed. The necessity for corrective lenses in essentially all people as they age imposes obvious financial costs. Safety and efficiency are also threatened when corrective lenses are not used for reasons of convenience, accessibility or cosmetic undesirability.

The etiology of presbyopia is not yet well defined, but changes in several tissues, including lens, zonules, and ciliary muscle, probably contribute to the progressive loss of accommodative ability. With age, the lens mass hardens, adhesion between the lens fibers increases, and the elasticity of the lens capsule decreases; the lens finally is unable to assume a more convex, accommodated shape despite maximal contraction of the ciliary muscle. The progressive rigidity of the lens is exacerbated by an apparent loss of refractivity of the lens tissue. The loss of refractive power in the lens tissue means that the age-impaired lens needs to assume a more convex shape for close focusing than does the lens of a younger person.

The progressive lens hardening and loss of refractive power appear to be inevitable with age. The prevailing view is currently that treatment of presbyopia is not feasible, except for the symptomatic prescribing of corrective glasses.

Age related changes in the zonules may also contribute to the development of presbyopia. With age, the location of zonule attachment to the lens capsule shifts from the lens equator onto the anterior surface of the crystalline lens. This apparently necessitates a greater movement of the ciliary muscle to produce a unit change of accommodation with age.

Although early studies suggested that changes in the ciliary muscle with age might contribute to the loss of accommodation, recent studies indicate that the ciliary muscle does not change substantially with age, but rather is relatively immobilized by its attachments to the lens, choroid and scleral spur.

The ciliary muscle controls the shape of the lens and thereby implements accommodation. Like most smooth muscles, the ciliary muscle has a dual innervation, receiving both sympathetic and parasympathetic fibers. In the ciliary muscle, the contraction necessary for accommodation is under parasympathetic (cholinergic) control, which clearly predominates. Opposing cholinergic control, the sympathetic (adrenergic) innervation, which plays a minor role, is responsible for relaxation of the ciliary muscle or inhibition of accommodation.

The role of sympathetic innervation in accommodation in humans has been the subject of several recent pharmacological investigations. The ciliary muscle can be made to "dilate" (the ciliary muscle ring widens) by alpha-adrenergic stimulation, which causes decreased accommodation. In one study, an alpha-adrenergic antagonist caused an average increase in accommodative amplitude of 1.5 D, which peaked 40 minutes after instillation and decayed rapidly to baseline in less than 2 hours. The effect appeared specifically related to alpha-adrenergic receptors in the ciliary muscle, rather than a non-specific effect on either pupil size or vasodilation of blood vessels.

The ciliary muscle also has beta-adrenergic receptors which, when stimulated, trigger ciliary muscle relaxation. Conversely, timolol, a beta-adrenergic antagonist has been reported to cause a net increase in tonic accommodation in unfocused eyes of a group of subjects with a mean age of 23. This effect has not been demonstrated in presbyopic patients.

Beta-adrenergic antagonists like timolol, betaxolol and levobunolol have been used topically to control elevated intraocular pressure. In this use, the beta-adrenergic antagonists appear to act by decreasing the rate of production of aqueous humor by the ciliary body.

There are no currently available treatments for presbyopia based on therapeutically manipulating the autonomic innervation of the ciliary muscle. In 1972, Eskridge reported a brief increase in the maximum accommodative response in a 36 year old subject treated with the parasympathomimetic drug eserine (Am. J. Optometry, August, 1972, pp. 632–635). A similar transient gain in accommodation was measured after treating subjects with the alpha-1 antagonist thymoxamine (Zetterstrom, Acta Ophthalmologica 65:699–704, 1987). The use of alpha-2 agonists was not suggested in these references.

No attempt has been made to utilize the accommodation-enhancing effect of parasympathomimetics or of sympatholytic drugs in any way for the treatment of presbyopia. Specifically, these drugs have not been used either to delay the onset of clinically evident presbyopia, or to treat clinically evident presbyopia in conjunction with concurrent use of corrective lenses.

SUMMARY OF THE INVENTION

According to the invention, a method for increasing the accommodative ability of an eye of a presbyopic subject is provided by treatment of the eye with an amount of a beta-adrenergic antagonist sufficient to increase the accomodative ability of the subject by at least 0.5 diopters. The treatment is intended in particular for subjects who are otherwise free of indications for ophthalmic treatments calling for a beta-adrenergic antagonist. In other words, treatment is given to subjects who do not exhibit, among other things, glaucoma or increased intraocular pressure.

The compound is administered in a pharmaceutically acceptable ophthalmic preparation. The compound may be administered topically by application of the compound to the eye, preferably in a non-irritating sterile solution or suspension. Preferably, the solution or suspension is at a pH compatible with the eye.

It is an object of the invention to provide means and method for increasing accommodation in presbyopes by topical treatment with beta-adrenergic antagonist compounds.

Other features and advantages of the invention will be apparent from the following description and from the claims.

DETAILED DESCRIPTION OF THE PREFERRED EMBODIMENTS

This invention encompasses therapeutic compounds and methods of treatment for decreasing the severity of clinically evident presbyopia. By clinically evident presbyopia, we mean a state of diminished accommodative ability characterized by discomfort or blurred vision when the affected person attempts to focus on nearby objects, for example fine print. The compounds and methods claimed increase the ability of the ciliary muscle to contract, and thus to change the curvature of the ocular lens, by decreasing the opposing muscle tone stimulated by sympathetic innervation.

While not limiting the treatment of this invention to the validity of one proposed mechanism of action, it is believed that the compounds of the invention may delay or relieve the symptoms of presbyopia by inhibiting the action of the sympathetically-stimulated components of the ciliary muscle, thereby sparing the parasympathetically-stimulated ciliary muscle components. The parasympathetically-stimulated components of the muscle control the tonic accommodation of the lens and contract to allow maximal accommodative ability; the sparing of these muscles by blocking their sympathetically-controlled muscle antagonists may delay or decrease presbyopic symptoms.

The compounds useful in practicing this invention are any beta-adrenergic antagonists. As used herein, the term beta-adrenergic antagonist means compounds that produce a net sympatholytic response, resulting in increased accomodation, by binding to beta-adrenergic receptors within the ciliary muscle of the eye. A sympatholytic response is characterized by the inhibition, diminishment, or prevention of the effects of impulses conveyed by the sympathetic nervous system.

The following proposed mechanism of action is described to illustrate one of the possible ways in which the methods and compounds of the invention influence the function of the ciliary muscle. The description of this mechanism is in no way intended to limit the scope of the invention to this particular mechanism. The beta-adrenergic antagonists of the invention bind to beta-adrenergic receptors on smooth muscles, including the ciliary muscle. The binding of the antagonists decreases beta-adrenergically mediated activity of adenylate cyclase within the smooth muscle cells, as well as decreasing calcium channel activity within the cell membranes. The resultant decreased cyclic AMP and calcium levels within the ciliary muscle cells may affect the contractility of the particular ciliary muscle components to which the beta-adrenergic antagonists bind. The end effect of the ocular treatment with the beta-adrenergic antagonists is decreased adrenergic tone, less relaxation of the ciliary muscle, and reduced opposition to cholinergically stimulated contraction.

Without limiting the invention to the specific groups and compounds listed, the following is a list of representative beta-adrenergic antagonists useful in this invention: Acebutolol (U.S. Pat. No. 3,857,952), Alprenolol (2 propanol, 1-[(1-methylethyl)amino]-3-[ 2-(2-propenyl)phenoxy]-hydrochloride, CAS-13707-88-5 and CAS-13655-52-2), Amosulalol (U.S. Pat. No. 4,217,305), Arotinolol (U.S. Pat. No. 3,932,400), Atenolol (U.S. Pat. Nos. 3,663,607 and 3,836,671), Befunolol (U.S. Pat. No. 3,853,923), Betaxolol (U.S. Pat. No. 4,252,984), Bevantolol (U.S. Pat. No. 3,857,891), Bisoprolol (U.S. Pat. Nos. 4,171,370 and 4,258,062), Bopindolol (U.S. Pat. No. 4,340,541), Bucumolol (U.S. Pat. No. 3,663,570), Bufetolol (U.S. Pat. No. 3,723,476), Bufuralol (U.S. Pat. No. 3,929,836), Bunitrolol (U.S. Pat. Nos. 3,940,489 and 3,961,071), Bunolol HCl (also known as levobunolol) 1(2H)-Naphthalenone, 5-[3-1,(1-dimethylethyl)amino}-2-hydroxypropoxy]-3,4-dihydro-, hydrochloride (±), CAS-31969-05-8 and CAS-27591-01-1; U.S. Pat. No. 3,649,691 and U.S. Pat. No. 4,463,176), Bupranolol (U.S. Pat. No. 3,309,406), Butidrine HCl (French Patent 1,390,056), Butofilolol (U.S. Pat. No. 4,252,825), Carazolol (German Patent 2,240,599), Carteolol (U.S. Pat. No. 3,910,924), Carvedilol (U.S. Pat. No. 4,503,067), Celiprolol (Urea, N'-[3-acetyl-4-[3-[1,1-dimethylethyl) amino]-2-hydroxypropoxy] pheynl]-N,N-diethyl-, monohydrochloride; CAS-57470-78-7 and CAS-56980-93-9), Cetamolol (U.S. Pat. No. 4,059,622), Cicloprolol HCl (2-propanol, 1-[4-[2-(cyclopropylmethoxy)ethoxy]-3-[ (1-methylethyl)amino]-, hydrochloride,(+); CAS-63686-79-3 and CAS-63659-12-1), Cloranolol (German Patent 2,213,044), Dexpropranolol (2-propanol, 1-[(1-methylethyl)-amino]-3-(1-naphthalenyloxy) hydrochloride; CAS-13071-11-9 and CAS-5051-22-9), Diacetolol HCl (acetamide , N-[3-acetyl-4- [2-hydroxy-3-[ (1-methylethyl )-amino] propoxy ] phenyl ]-, monohydrochloride; CAS-69796-04-9 and CAS-22568-64-5) , Dilevalol (racemate Labetalol; ([R-(R,R)]-2-hydroxy-5-[ 1-hydroxy-2-[(1-methyl-3-phenylpropyl)amino]ethyl]

benzamide 4-methylbenzenesulfonate salt); CAS-75659-08-4 and CAS-75659-07-3), Epanolol (U.S. Pat. No. 4,167,581), Esmolol (U.S. Pat. No. 4,387,103), Exaprolol (2-propanol, 1-(2-cyclohexylphenoxy)-3-[(1-methylethyl)amino]-, hydrochloride, (±); CAS-59333-90-3 and CAS-55837-19-9), Flestolol Sulfate (benzoic acid, 2-fluoro-, 3-[[2-[(aminocarbonyl)amino]-1,1-dimethylethyl] amino]-2-hydroxypropyl ester, (±), sulfate; CAS-88844-73-9 and CAS-87721-62-8), Indenolol (U.S. Pat. No. 4,045,482), Labetalol (U.S. Pat. No. 4,012,444), Mepindolol (Swiss Patents 469,002 and 472,404), Metalol HCl (methanesulfonamide, N-[4-[1-hydroxy-2-(methylamino)propyl]phenyl]-monohydrochloride) CAS-955-48-6 and CAS-7701-65-7, Metoprolol (U.S. Pat. No. 3,873,600), Moprolol (U.S. Pat. No. 3,501,769), Nadolol (U.S. Pat. No. 3,935,267), Nadoxolol (U.S. Pat. No. 3,819,702), Nifenalol (British Patent 950,682), Nipradilol (U.S. Pat. Nos. 4,394,382 and 4,727,085), Oxprenolol (Belgium Patent 669,402), Pamatolol Sulfate (carbamic acid, [2-[4-[2-hydroxy-3-[(1-methylethyl amino ] propoxy] phenyl ]- ethyl]-, methyl ester, (±), sulfate. CAS-59954-01-7 and CAS-59110-35-9), Penbutolol (U.S. Pat. No. 3,551,493), Pindolol (Swiss Patents 469,002 and 472,040), Practolol (U.S. Pat. No. 3,408,387), Pronethalol (British Patent 909,357), Propranolol (U.S. Pat. Nos. 3,337,628 and 3,520,919), Sotalol (Methanesulfonamide, N-[4-[1-hydroxy-2-[(1methylethyl) amino] ethyl ] phenyl ]-,monohydrochloride; CAS-959-24-0 and CAS-3930-20-9), Sulfinalol (German Patent 2,728,641), Talinolol (U.S. Pat. Nos. 3,935,259 and 4,038,313), Tertatolol (U.S. Pat. No. 3,960,891), Timolol (U.S. Pat. Nos. 3,655,663 and 3,657,237), Tiprenolol HCl (2-Propanol,1-[(1-Methylethyl)amino]-3-[ 2-(methylthio)phynoxy]-, hydrochloride; CAS-39832-43-4 and CAS-26481-51-6), Tolamolol (Benzamide, 4-[2-[[2-hydroxy-3-(2-methylphenoxy)-propyl] amino ethoxy ] CAS-38103-61-6), Toliprolol (U.S. Pat. Nos. 3,432,545 and 3,459,782), and Xibenolol (U.S. Pat. No. 4,018,824).

Analogs of the foregoing compounds that function as beta-adrenergic antagonists also are specifically intended to be embraced by the invention. The ability of such analogs to increase accommodation according to the invention can be tested easily using no more than routine experimentation.

The therapy is suited in particular for subjects who are otherwise free of indications for ophthalmic treatments calling for a beta-adrenergic antagonist. It should be understood by those of ordinary skill in the art that there currently are ophthalmic conditions that are treated using beta-adrenergic antagonists. For example, elevated intraocular pressure can be advantageously treated with compounds having beta-adrenergic antagonist activity. By "elevated intraocular pressure", it is meant an abnormally high pressure of the fluid within the eye. By "free of indications", it is meant that the subject does not have symptoms or a clinical history that call for topical treatment of the eye with a beta-adrenergic antagonist (other than the indications which exist as a result of this invention), and that the subject also is free of symptoms or a clinical history that call for topical treatment of the eye with another adrenergically-active compound which has significant beta-adrenergic antagonist activity.

The beta-adrenergic antagonists of the invention may be administered per se (neat) or in the form of a pharmaceutically acceptable salt. When used in medicine, the salts of the beta-adrenergic antagonists should be both pharmacologically and pharmaceutically acceptable, but non-pharmaceutically acceptable salts may conveniently be used to prepare the free active compound or pharmaceutically acceptable salts thereof. Pharmacologically and pharmaceutically acceptable salts include, but are not limited to, those prepared from the following acids: hydrochloric, hydrobromic, sulphuric, nitric, phosphoric, maleic, acetic, salicyclic, p-toluenesulfonic, tartaric, citric, methanesulphonic, formic, malonic, succinic, naphthalene-2-sulphonic, and benzenesulphonic. Also, pharmaceutically acceptable salts can be prepared as alkaline metal or alkaline earth salts, such as sodium, potassium or calcium salts of the carboxylic acid group. Thus, the present invention provides pharmaceutical formulations which comprise beta-adrenergic antagonists together with one or more pharmaceutically acceptable carriers and optionally other therapeutic ingredients. The carrier(s) and other ingredients of course must be pharmaceutically acceptable. Such formulations preferably contain the beta-adrenergic antagonist in pharmaceutically effective concentrations and amounts and most preferably are in formulations and containers adapted for topical delivery.

Certain of the compounds of the invention are known for use in the art for other purposes, and are known to be safe under ordinary conditions of use. Thus, the treatment of this invention can be administered by substantially conventional means, consistent with known eye treatments and while avoiding irritation, discomfort or the need for unusual application procedures. The commercially available beta-adrenergic antagonists have reasonable shelf life and can be packaged, stored and transported for ophthalmic use without unusual difficulty or cost.

Formulations of the invention include any formulation in which the compounds of the invention may be delivered to the eye. Preferably, the beat-adrenergic antagonists of the invention are applied to the eye in a topical preparation. By a topical preparation, it is meant a preparation which is adapted to be applied to the surface of the eye. In such a preparation, the therapeutic compounds of the preparation contact the surface of the eye, and penetrate into the deeper tissues of the eye. Such preparations usually have liquid carriers which can be aqueous solutions or suspensions.

The compounds of the invention may be applied in a pharmaceutically acceptable ophthalmic preparation, meaning a preparation which produces medically desirable therapeutic effects without concurrently causing clinically significant adverse effects. Clinically significant side effects refer to unacceptable side effects of the preparation, including either medically or cosmetically unacceptable effects. Examples of unacceptable side effects include reddened or irritated eyes, or impaired long distance vision.

The compounds of the invention are administered in therapeutically effective amounts. A therapeutically effective amount is one which causes medically useful increase in accommodative ability of a presbyopic eye. Such an increase is at least 0.5 and preferably one diopter. The compounds are typically added to the ophthalmic preparations of the invention at concentrations of 0.01–10% by weight of the entire composition.

In the preferred embodiments, the compounds of the invention are administered topically, delivered in a medically acceptable, substantially sterile, nonirritating ophthalmic preparation. The ophthalmic preparations may routinely contain pharmaceutically acceptable concentrations of salts, buffering agents, preservatives, viscosity modifiers, osmotic agents, and delivery enhancing agents.

Salts which can be used include but are not limited to sodium chloride, zinc sulfate, and potassium chloride. Buffers which can be used include but are not limited to boric acid and citric acid. Preservatives which can be used include but are not limited to benzalkonium chloride and edetate disodium. Viscosity modifiers which can be used include but are not limited to methyl cellulose, glycerol, and polyethylene glycol. Osmotic agents which can be used include but are not limited to mannitol and sorbitol. Delivery enhancing agents that facilitates the delivery of the therapeutic compound of the invention into the aqueous humor, include substances which increase corneal permeability, such as surfactants, wetting agents, liposomes, DMSO, and the like. A wetting agent is a substance which facilitates corneal penetration by mildly disrupting the outer corneal surface. A preferred wetting agent is benzalkonium chloride. Other examples of wetting agents include sorbitan esters, and polyoxyethylene ethers.

It should be understood that although specific formulations have been defined, many variations are possible. In all cases, the ophthalmic formulations useful in the eye are nonirritating and nondamaging to the eye in the preferred form, and are effective to provide the results desired. Normally, such formulations can be applied in a liquid carrier, with an aqueous carrier being preferred although in some instances, quick dissolving forms of the medicaments may be administered in powder form or rubbed into the eye from applicators of various types. Spraying of the eye, eyedrops, and other methods of application can be used.

Dosage levels will vary greatly depending upon the individual to be treated and the specific medicament used. Proper dosing can be determined without undue experimentation and according to procedures well known to those of ordinary skill in the art.

Humans are characterized by a mean amplitude of accommodation (measured in diopters) that decreases steadily with age. The methods of this invention are useful with subjects having a maximal dioptric power of 10 or less, preferably with subjects having a maximal dioptric power of 6 or less, and most preferably with subjects having a maximal dioptric power of 4 or less.

The preparations are preferably to be packaged as sterile solutions in dropper bottles, as are well known in the trade. Other containers, including eye cups, can also be used. The preparation is preferably packaged with instructions for using the preparation in treating presbyopia, typically directing the user of the preparation to administer 1 to 2 drops of the solution to each eye.

In a specific example of this invention, a base solution can be formulated as follows: Sodium Chloride 0.3%; Edetate Disodium 0.1%; Boric Acid 1.0%; Benzalkonium Chloride 0.01% Sodium Hydroxide (adjust to pH 6.4) and Water. Timolol, at a concentration of 0.5% weight/volume, is added to the base solution.

The above-formulation is administered to the eye of a fifty year old human adult with presbyopia, shown by his discomfort when reading, or his inability to read fine print. Vision is improved after administration of the eye drops.

When other beta-adrenergic antagonists are substituted for Timolol, similar results are obtained.

EQUIVALENTS

It should be understood, however, that the foregoing description of the invention is intended merely to be illustrative by way of example only and that other modifications, embodiments, and equivalents may be apparent to those skilled in the art without departing from its spirit.

I claim:

1. A method for increasing the accommodative ability of a presbyopic subject, comprising administering to the subject a beta-adrenergic antagonist in an amount sufficient to increase the accomodative ability of the subject by at least 0.5 diopters.

2. The method of claim 1 wherein the beta-adrenergic antagonist is administered topically to the eye in a pharmaceutically acceptable ophthalmic preparation.

3. The method of claim 2 wherein the beta-adrenergic antagonist is administered to a subject that is otherwise free of indications for ophthalmic beta-adrenergic antagonist treatment.

4. The method of claim 2 wherein the beta-adrenergic antagonist is administered to a subject that is free of elevated intraocular pressure.

5. The method of claim 3 wherein the beta-adrenergic antagonist is selected and is administered in an amount Whereby the treatment is free of clinically significant adverse effects on the visualization of distance objects.

6. The method of claim 3 wherein the beta-adrenergic antagonist is selected and is administered in an amount whereby the treatment is free of medically unacceptable side effects.

7. The method of claim 1 wherein the beta-adrenergic antagonist is selected from the group consisting of:

Acebutolol, Alprenolol, Amosulalol, Arotinolol, Atenolol, Befunolol, Betaxolol, Bevantolol, Bisoprolol, Bopindolol, Bucumolol, Bufetolol, Bufuralol, Bunitrolol, Bunolol HCl, Bupranolol, Butidrine HCl, Butofilolol, Carazolol, Carteolol, Carvedilol, Celiprolol, Cetamolol, Cicloprolol HCl Cloranolol, Dexpropranolol, Diacetolol HCl, Dilevalol, Epanolol, Esmolol, Exaprolol, Flestolol Sulfate, Indenolol, Labetalol, Mepindolol, Metalol HCl, Metoprolol, Moprolol, Nadolol, Nadoxolol, Nifenalol, Nipradilol, Oxprenolol, Pamatolol Sulfate, Penbutolol, Pindolol, Practolol, Pronethalol, Propranolol, Sotalol, Sulfinalol, Talinolol, Tertatolol, Timolol, Tiprenolol HCl, Tolamolol, Toliprolol, and Xibenolol.

8. The method of claims 1 or 3 wherein the beta-adrenergic antagonist is Acebutolol.

9. The method of claims 1 or 3 wherein the beta-adrenergic antagonist is Alprenolol.

10. The method of claims 1 or 3 wherein the beta-adrenergic antagonist is Amosulalol.

11. The method of claims 1 or 3 wherein the beta-adrenergic antagonist is Arotinolol.

12. The method of claims 1 or 3 wherein the beta-adrenergic antagonist is Atenolol.

13. The method of claims 1 or 3 wherein the beta-adrenergic antagonist is Befunolol.

14. The method of claims 1 or 3 wherein the beta-adrenergic antagonist is Betaxolol.

15. The method of claims 1 or 3 wherein the beta-adrenergic antagonist is Bevantolol.

16. The method of claims 1 or 3 wherein the beta-adrenergic antagonist is Bisoprolol.

17. The method of claims 1 or 3 wherein the beta-adrenergic antagonist is Bopindolol.

18. The method of claims 1 or 3 wherein the beta-adrenergic antagonist is Bucumolol.

19. The method of claims 1 or 3 wherein the beta-adrenergic antagonist is Bufetolol.

20. The method of claims 1 or 3 wherein the beta-adrenergic antagonist is Bufuralol.

21. The method of claims 1 or 3 wherein the beta-adrenergic antagonist is Bunitrolol.

22. The method of claims 1 or 3 wherein the beta-adrenergic antagonist is Bunolol HCl.

23. The method of claims 1 or 3 wherein the beta-adrenergic antagonist is Bupranolol.

24. The method of claims 1 or 3 wherein the beta-adrenergic antagonist is Butidrine HCl.

25. The method of claims 1 or 3 wherein the beta-adrenergic antagonist is Butofilolol.

26. The method of claims 1 or 3 wherein the beta-adrenergic antagonist is Carazolol.

27. The method of claims 1 or 3 wherein the beta-adrenergic antagonist is Carteolol.

28. The method of claims 1 or 3 wherein the beta-adrenergic antagonist is Carvedilol.

29. The method of claims 1 or 3 wherein the beta-adrenergic antagonist is Celiprolol.

30. The method of claims 1 or 3 wherein the beta-adrenergic antagonist is Cetamolol.

31. The method of claims 1 or 3 wherein the beta-adrenergic antagonist is Cicloprolol HCl Cloranolol.

32. The method of claims 1 or 3 wherein the beta-adrenergic antagonist is Dexpropranolol.

33. The method of claims 1 or 3 wherein the beta-adrenergic antagonist is Diacetolol HCl.

34. The method of claims 1 or 3 wherein the beta-adrenergic antagonist is Dilevalol.

35. The method of claims 1 or 3 wherein the beta-adrenergic antagonist is Epanolol.

36. The method of claims 1 or 3 wherein the beta-adrenergic antagonist is Esmolol.

37. The method of claims 1 or 3 wherein the beta-adrenergic antagonist is Exaprolol.

38. The method of claims 1 or 3 wherein the beta-adrenergic antagonist is Flestolol Sulfate.

39. The method of claims 1 or 3 wherein the beta-adrenergic antagonist is Indenolol.

40. The method of claims 1 or 3 wherein the beta-adrenergic antagonist is Labetalol.

41. The method of claims 1 or 3 wherein the beta-adrenergic antagonist is Mepindolol.

42. The method of claims 1 or 3 wherein the beta-adrenergic antagonist is Metalol HCl.

43. The method of claims 1 or 3 wherein the beta-adrenergic antagonist is Metoprolol.

44. The method of claims 1 or 3 wherein the beta-adrenergic antagonist is Moprolol.

45. The method of claims 1 or 3 wherein the beta-adrenergic antagonist is Nadolol.

46. The method of claims 1 or 3 wherein the beta-adrenergic antagonist is Nadoxolol.

47. The method of claims 1 or 3 wherein the beta-adrenergic antagonist is Nifenalol.

48. The method of claims 1 or 3 wherein the beta-adrenergic antagonist is Nipradilol.

49. The method of claims 1 or 3 wherein the beta-adrenergic antagonist is Oxprenolol.

50. The method of claims 1 or 3 wherein the beta-adrenergic antagonist is Pamatolol Sulfate.

51. The method of claims 1 or 3 wherein the beta-adrenergic antagonist is Penbutolol.

52. The method of claims 1 or 3 wherein the beta-adrenergic antagonist is Pindolol.

53. The method of claims 1 or 3 wherein the beta-adrenergic antagonist is Practolol.

54. The method of claims 1 or 3 wherein the beta-adrenergic antagonist is Pronethalol.

55. The method of claims 1 or 3 wherein the beta-adrenergic antagonist is Propranolol.

56. The method of claims 1 or 3 wherein the beta-adrenergic antagonist is Sotalol.

57. The method of claims 1 or 3 wherein the beta-adrenergic antagonist is Sulfinalol.

58. The method of claims 1 or 3 wherein the beta-adrenergic antagonist is Talinolol.

59. The method of claims 1 or 3 wherein the beta-adrenergic antagonist is Tertatolol.

60. The method of claims 1 or 3 wherein the beta-adrenergic antagonist is Timolol.

61. The method of claims 1 or 3 wherein the beta-adrenergic antagonist is Tiprenolol HCl.

62. The method of claims 1 or 3 wherein the beta-adrenergic antagonist is Tolamolol.

63. The method of claims 1 or 3 wherein the beta-adrenergic antagonist is Toliprolol.

64. The method of claims 1 or 3 wherein the beta-adrenergic antagonist is Xibenolol.

\* \* \* \* \*